United States Patent

Holmes

[11] Patent Number: 5,951,554
[45] Date of Patent: Sep. 14, 1999

[54] SCREW REMOVAL SYSTEM

[76] Inventor: Russell P. Holmes, 201 Newbury St., Apt. #405, Boston, Mass. 02116

[21] Appl. No.: 08/944,936

[22] Filed: Oct. 2, 1997

[51] Int. Cl.$^6$ .................................................. A61B 17/56
[52] U.S. Cl. .............................. 606/61; 606/60; 606/62; 606/63
[58] Field of Search ................................ 606/61, 60, 62, 606/63

[56] References Cited

U.S. PATENT DOCUMENTS

| | | | |
|---|---|---|---|
| 1,683,796 | 9/1928 | Pearce | 606/61 |
| 3,106,233 | 10/1963 | Wolny | 145/1 |
| 4,688,315 | 8/1987 | Jannke | 606/61 |
| 5,643,259 | 7/1997 | Sasso et al. | 606/61 |

Primary Examiner—Michael Buiz
Assistant Examiner—(Jackie) Tan-Uyen Thi Ho

[57] ABSTRACT

A screw removal system is provided that can be used to remove a broken screw piece, which is embedded in a bone. The screw removal system includes an internally-threaded outer tube and a T-handled shaft which screws into the tube. The outer tube includes at one end two flange legs that engage the second or third thread of the broken screw piece and a bonding component sized to engage the broken screw piece. With the outer tube held in a stationary position by a wrench, the T-handled shaft is rotated downwardly to force the flange legs, and the bonding component into a locking engagement with the broken screw piece. After this locking engagement is achieved, the outer tube wrench is held so that it can rotate with the T-handled shaft and the broken screw piece can be unscrewed out of the bone upon continued rotation of the T-handled shaft, which causes the rotation of both the outer tube and the engaged screw piece.

10 Claims, 2 Drawing Sheets

SCREW REMOVAL SYSTEM

FIELD OF THE INVENTION

This invention relates generally to medical instruments for use in removal of surgically-implanted screws from cancellous bone. Particularly, the invention relates to removal of broken screws from the bone.

BACKGROUND OF THE INVENTION

Screws and other mechanical connecting parts are often surgically implanted in a patient to connect pieces of bone which are broken or weak due to injury or disease. A variety of occasions arise in which these screws and/or parts must later be removed. For example, screws may be surgically removed after the desired healing is achieved, or when the bone is not healing as expected, or in cases in which the screw was not oriented properly when first implanted by the surgeon. In still other cases, a screw implanted in a patient's spine may be pressing upon a nerve and causing the patient pain. The screw may thus need to be removed. Such screws, however, may have broken due to weakness in the screw as a result of repeated flexing and/or shock. In this instance, the broken screw pieces would thus need to be removed.

Various instruments for the removal of screws from bone have been known and described. A review of the art reveals that such instruments engage the head of the screw in order to remove the screw from the bone by an action applied by the instrument to the head of the screw. Typically, the screw head is engaged by a specially-designed tool which is used to rotate the screw or otherwise apply a force sufficient to retract the screw from the bone. The tool is designed to mate with the head of the screw. For example, in some cases, the screw head will have a corresponding socket formation to accommodate an Allen wrench or Phillips screw driver.

As noted, there are many occasions, however, in which a screw breaks, typically due to weakness from repeated flexing and/or shock. In that case, the remaining broken pieces of the screw cannot be removed with conventional tools which operate by driving engagement with the screw head, because the screw head has broken off. Thus, such tools, which are generally designed to mate with the screw head, cannot function and are completely ineffective if the screw head has broken off.

In addition, screw fragments can be lodged deep in bone and yet, it is desirable to remove as little bone as possible when removing the fragments.

There remains a need, therefore, for a device which can be used to remove a broken screw piece from the bone. There remains a need for such a device which does not require the head of the screw to be intact on the screw. There is a further need for a screw piece removal device which involves removal of as little bone as possible and which maintains the mechanical advantage of a comparatively long handle in that it has advantageous gripping action and is easily directed by a surgeon.

SUMMARY OF THE INVENTION

The present invention is a broken screw removal system which includes an internally reverse-threaded outer tube with two flanges on one end thereof which are positioned to engage the threads of the broken, headless screw piece. A bonding component, such as a generally cubical bud with an optional interference surface, can be positioned in the tube such that the interference surface is compressed down upon the broken screw piece. The surface envelopes the proximal end of the broken screw piece by the action of rotating a threaded T-handled shaft which threads into the outer tube. The bonding component forms a tight engagement between the screw removal assembly and the broken screw piece to allow for ultimate removal of the broken screw piece.

More specifically, in order to remove a broken screw, the area of bone around the screw is hollowed out by a conventional trephining process. Then, the outer tube is driven down into the bone toward the broken screw piece and rotated several times to slide the flanges around the first several threads on the broken screw piece. Then, the outer tube is held stationary by a suitable wrench. The T-handled shaft is thereafter threadedly advanced by rotation in a first direction, which will typically be counterclockwise, down the outer tube, while the outer tube is held by a wrench. The T-handled shaft is thus used to place the flanges of the outer tube into direct engagement with the threads of the broken screw piece such that the flanges are compressed against the threads of the broken screw piece.

Additionally, to provide a further locking engagement between the outer tube and the broken screw piece, the bonding component, which may be fixedly positioned within the tube proximate to the flanges, compresses upon the upper-most end of the broken screw piece. The bonding component is compressed tightly against the screw piece. The interference surface of the bonding component may also include dagger or blade extensions which will jam into and provide an interference with the upper threads of the broken screw piece. This interference provides a tight engagement and, thus, forms a bond between the shaft-tube assembly and the broken screw piece. Alternatively, other configurations may be used for the bonding component or the interference surface, as desired.

When the T-handled shaft has been sufficiently advanced along the threading of the outer tube to achieve this locking engagement, the wrench is held such that the outer tube can also rotate with the turning of the T-handled shaft. At this point, continued counterclockwise rotation of the T-handled shaft and the outer tube together, while the broken screw piece is in a tight engagement with the outer tube, will cause the broken screw piece to be unscrewed and retracted from the bone.

BRIEF DESCRIPTION OF THE DRAWINGS

The foregoing discussion will be understood more readily from the following detailed description of the invention when taken in conjunction with the accompanying drawings, in which.

DETAILED DESCRIPTION OF THE PREFERRED EMBODIMENTS

Figure 1:
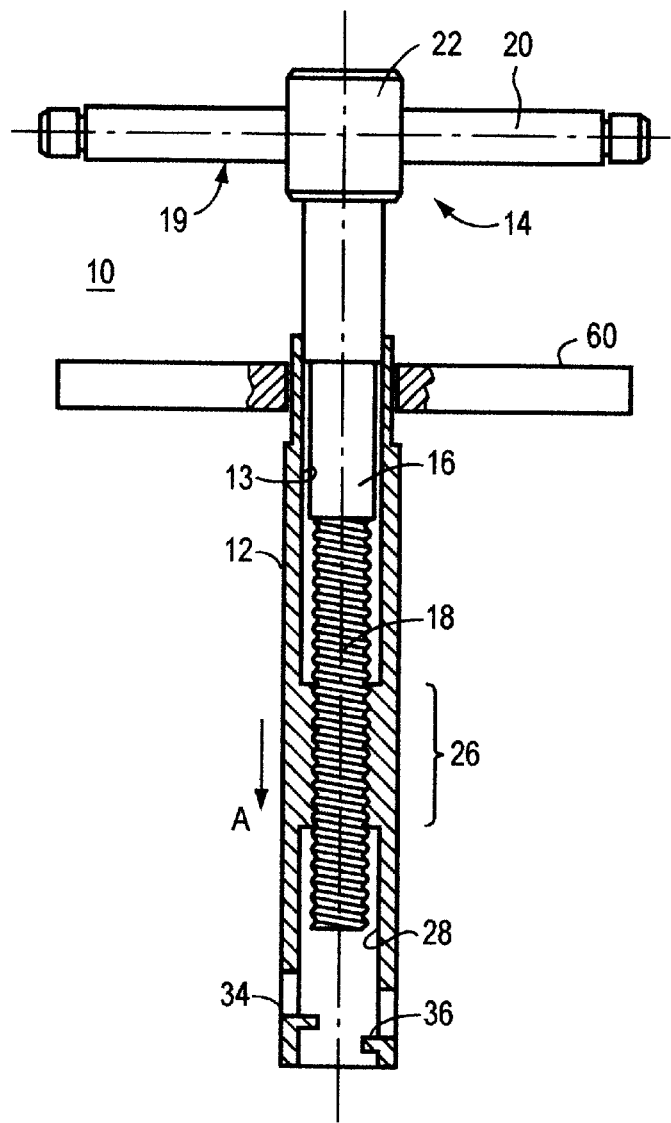
FIG. 1 is an elevational view of the screw removal system of the present invention with one portion of the outer tube cut away for depicting the T-handled shaft screwed into the outer tube.

FIG. 1 illustrates a screw removal system 10 embodying the present invention. The screw removal system 10 includes an outer tube 12 having a cylindrical internal wall 13. A portion 26 of the internal wall 13 is reverse-threaded. Two flanges 34 and 36 are located at one end of the tube 12. As described herein, the flanges 34 and 36 are positioned at one end of the tube 12 to engage the threads of a broken screw piece which is to be removed from a bone.

The outer tube 12 is sized to receive a threaded T-shaped handle assembly 14. The threaded T-shaped handle assembly 14 has a shaft 16 with threads 18. A gripping handle 19 is manipulated by turning a bar 20 which rotates the entire assembly 14. T-shaped handle assembly 14 is preferably constructed such that an axial member 22 has a hollowed out portion through which turning bar 20 is passed. Turning bar 20 can then be rotated to advance the shaft 16 down into the outer tube 12.

The threads 18 of the shaft 16 are of a direction of helical advance opposite to that of the direction helical advance of threads 26 of the tube wall 13. In this way, when the handle assembly 14 is turned counterclockwise, for example, it will be advanced down the tube in the direction shown by arrow A in FIG. 1. The outer tube 12 can be held in a stationary position by a wrench 60 or other suitable device. Preferably, wrench 60 can slide down over two flattened sections 62 and 64 of tube 12 which can be machined into the tube 12. When in this position, the wrench 60 can be held to maintain tube 12 in a stationary position with respect to the handle assembly 14. When the T-shaped handle assembly 14 is rotated in a first direction, typically counterclockwise, with the outer tube 12 held stationary by wrench 60, the T-shaped handle assembly 14 advances down the tube 12.

The housing of outer tube 12 (FIG. 2) has a bend 32 which is machined into the wall of the tube 12. The bend 32 establishes a flange 34 (FIG. 1). When removing a broken screw piece, the outer tube 12 is positioned in the bone in proximity to the screw piece and is then rotated several times until the flange 34 engages a thread several threads down on the broken screw piece.

Figure 2:
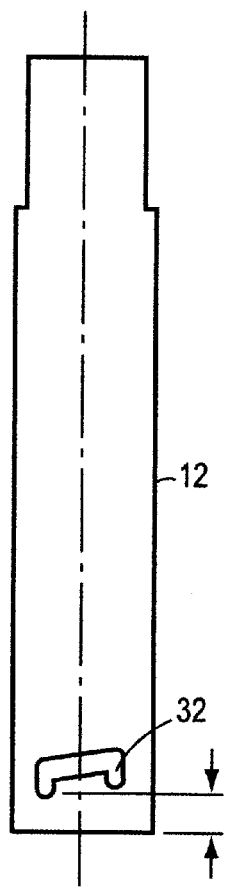
FIG. 2 is a side elevational view of the outer tube of the present invention.

Similarly, a bend in the opposite side of the tube 12, which opposite side is not visible in FIG. 2, establishes a flange 36 shown in FIG. 1. This flange 36 engages the next thread on the broken screw piece. In this manner, the outer tube 12 can be placed in direct engagement with a broken screw piece.

Figure 3:
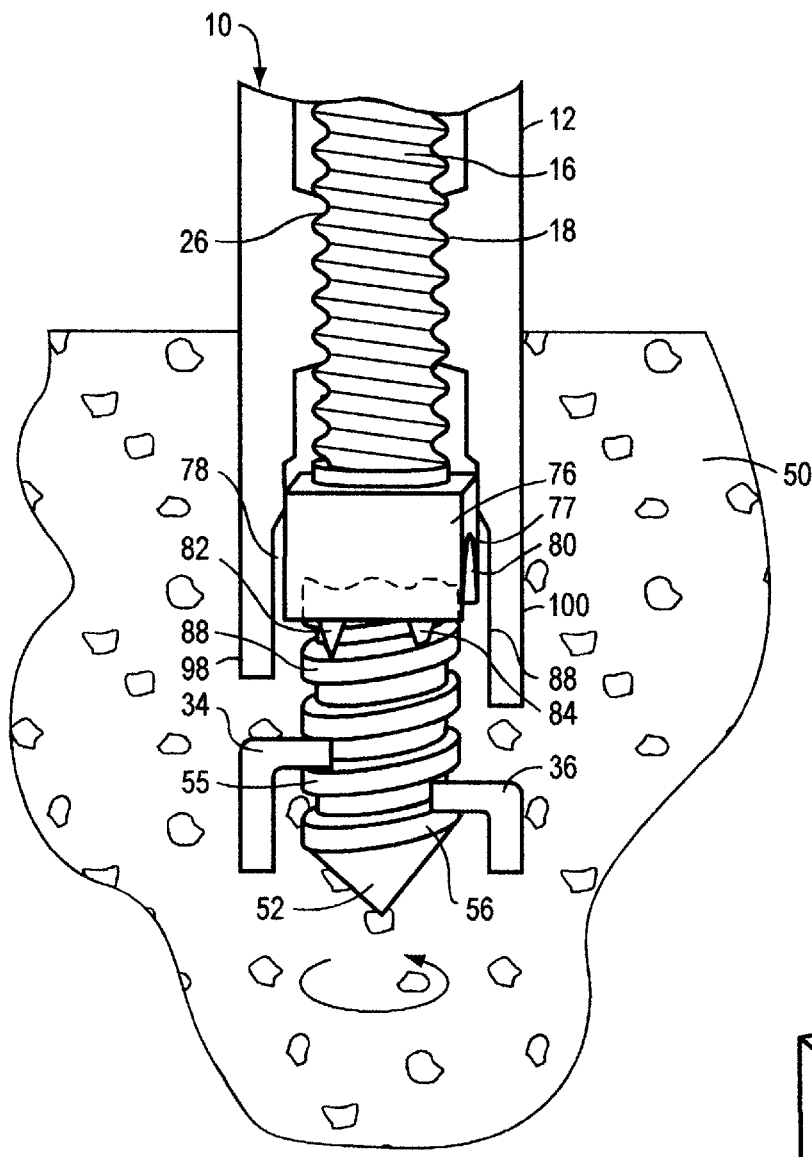
FIG. 3 is an elevational view of the screw removal system with the outer wall of the outer tube cut away and with the screw removal system engaging a broken screw piece embedded in bone.

More specifically, the operation of the screw removal system 10 of the present invention can be further understood with reference to FIG. 3. FIG. 3 shows a portion of bone 50 having a broken screw piece 52 embedded therein. Before a removal procedure, the area around the bone is trephined in a conventional manner in order to loosen the bone around the broken screw piece 52.

Once the bone around the screw piece is loosened, the outer tube 12 of the screw removal system 10 is placed down into the bone in the proximity of the screw piece and rotated until the flanges 34 and 36 engage two of the threads designated by reference characters 55 and 56 (FIG. 3) of the broken screw piece 52. In order to ascertain that the outer tube 12 is in such a position, the surgeon may apply an outward tug on the tube to verify that the flanges 34 and 36 are around the threads 55 and 56 in which case the tube 12 cannot be easily pulled back out of the bone.

Turning bar 20 (FIG. 1) is then rotated in a first direction, typically counterclockwise, and the handle shaft 16 is screwed down into the tube 12 as threads 18 of the shaft 16 engage the threads 26 of tube 12. The advancing of the T-handled shaft assembly 14, with the outer tube 12 held in its stationary by a wrench 60 (FIG. 1), forces the flanges 34 and 36 to be compressed upon and to squeeze the threads 55 and 56, respectively, of the broken screw piece 52.

Figure 4:
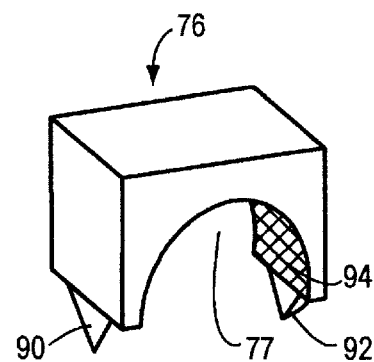
FIG. 4 is an elevational view of the bonding component of the present invention.

In order to provide a locking engagement between the broken screw piece 52 on the one hand, and the T-handled shaft assembly 14 and the outer tube 12 on the other hand, it is preferred to provide a bonding component 76 which is shown more particularly in FIG. 4. The bonding component 76 is generally a cubical bud with a recessed surface 77 contoured to encompass a proximal end of a broken screw piece. It is preferably fixedly disposed within the tube 12 either due to its shape, or alternatively, the side portions 98 and 100 of tube 12 can be squeezed inwardly to tightly hold component 76 within the tube 12.

Referring again to FIG. 3, the broken screw piece 52 has broken end 80. The interference surface 77 of the bonding component 76 is placed down over and encompassing broken end 80. Upon the rotation and thus the compression by shaft 16, surface 77 compresses down on the screw piece 52 to squeeze it upon flanges 34 and 36. In addition, bonding component 76 can be provided with dagger components 82 and 84, or blades 90 and 92 (FIG. 4). The dagger components 82 and 84 provide an interference, such as a notch, in the thread 88 and thus distort screw thread 88 which the dagger engages. The overall action of the flanges 34 and 36, the bud 76 and the daggers 82 and 84 results in the deformation of thread 88 and threads 55 and 56 as shown in FIG. 3. The interference and deformation of the screw threads 88 and 55 and 56 provides a tight, locked engagement between the bonding component 76, which is fixedly held in the outer tube 12 and the screw piece 52.

When the tight engagement is achieved by the bonding component 76 engaging the broken screw piece 52, the system 10 will not slip off the broken screw piece 52 upon the counterclockwise rotation of the assembly 10 when removing the screw piece.

There may be a number of different configurations of the bonding component which can be provided while remaining within the scope of the present invention. For example, the bonding component can be readily adapted such that the lower portion can include blades 90 and 92 (FIG. 4) as part of the interference surface 77, to provide interference with the threads of the broken screw piece 52. In addition, a cross hatching such as pattern 94 may be provided on either of the sides of bonding component 76, or the surface 77 which encompasses the broken screw piece. The rough surface would thus also contribute to a tight locking compression between bonding component 76 and the screw piece 52. In such a case, the surface 77 would be flat and, preferably, not recessed. The cross hatching 94 engages the proximal end 80 of the screw piece 52 and provides interference with the end 80.

After the locking engagement has been achieved such that the broken screw piece 52 is being held tight by means of bonding component 76 and flanges 34 and 36, the wrench 60 is then held such that the outer tube 12 is also rotated with the T-handle shaft assembly 14. In this way, the T-handle turning bar 20 and the wrench 60 are turned simultaneously. Continued rotation of the entire screw removal system 10, which includes the screw piece tightly and permanently attached to the bonding component 76, in the counterclockwise direction, designated by the arrow B in FIG. 3, thus causes the screw piece 52, which has threading of a direction which is the same as that of the shaft 16, to unscrew out of the bone. Thus, the system 10 with the broken screw piece 52 attached is rotated outwardly and extracted out of bone 50.

It should be understood, therefore, that the present invention provides a screw removal system which effectively removes broken screw pieces which do not have a screw head which can be engaged by a tool. The device of the present invention can be used with any type of screw, even screws with unconventional heads that require special tools for insertion and removal. Thus, the device can be utilized to remove any type of broken screw piece. The system can be readily used with an accompanying conventional trephining process and it involves minimal bone removal. The screw removal system is low cost and easy to manufacture.

The terms and expressions employed herein are used as terms of description and not of limitation and there is no intention in the use of such terms and expressions, of excluding any equivalents of the features shown and described or portions thereof, but it is recognized that various modifications are possible within the scope of the invention claimed.

What is claimed is:

1. A screw removal system for removing a broken screw piece that is embedded in bone, with a bone area around said screw piece having been loosened by a trephining process, the screw removal system comprising:

(A) a rotatable shaft, a portion of said shaft being threaded; and (B) an outer tube having a cylindrical internal wall, and said outer tube being insertable into said bone in proximity to said broken screw piece within said loosened bone area, and said tube further being sized to receive said rotatable shaft, said outer tube further including:

(i) a threaded portion along said cylindrical internal wall for threaded engagement with said rotatable shaft, such that rotation of said rotatable shaft in a first direction with respect to said outer tube, advances said rotatable shaft along said outer tube, and (ii) locking means internally disposed and substantially confined within one end of said outer tube, and contoured to engage at least one thread of said broken screw piece and being capable of being tightened onto said broken screw piece upon compression induced by rotation of said shaft into said outer tube to provide a tight engagement between said tube and said broken screw piece, whereby upon said outer tube being released to said freely rotating position, continued rotation of said rotatable shaft in said first direction extracts said broken screw piece from said bone.

2. The screw removal system of claim 1 wherein said locking means includes at least one flange extending into said tube from said internal wall of said tube, said flange engaging a thread of said broken screw piece and being compressed thereupon when said shaft is advanced along said tube, without extending substantially further into said bone than said tube extends whereby said compressed flange establishes said tight engagement between said tube and said broken screw piece and continued rotation of said shaft with simultaneous rotation of said outer tube extracts said broken screw piece from said bone.

3. The screw removal system of claim 1 wherein said locking means includes a bonding component disposed within said tube such that it will engage a proximal end of said broken screw piece to establish said tight engagement between said tube and said broken screw piece.

4. The screw removal system of claim 3 wherein said bonding component includes interference means disposed on said bonding component such that said interference means deforms at least one thread of said broken screw to provide an even tighter engagement between said tube and said broken screw piece.

5. The screw removal system of claim 4 wherein said bonding component is fixed within said tube such that it cannot rotate within the tube, but can only move downwardly when said rotatable shaft is advanced along said outer tube.

6. The screw removal system of claim 5 wherein said outer tube has two flat portions proximate to said flanges to tightly hold said bonding component to resist rotation of said bonding component.

7. The screw removal system of claim 2 wherein said locking means includes a first and a second flange disposed opposite one another on said internal wall of said tube, and said flanges being formed by bends in said wall of said tube, said bends being turned inwardly to form said first and second flanges.

8. The screw removal system of claim 1 wherein said threading of said T-handled shaft is of a direction of helical advance which is opposite to that of the threading of said internal wall of said tube, but which direction is the same as the direction of helical advance of said broken screw piece.

9. The screw removal system of claim 4 wherein said interference means is a component selected from the group consisting of daggers, blades and cross hatched surfaces.

10. The screw removal system of claim 1 wherein said shaft has a T-handle for rotating the shaft into said outer tube.

* * * * *